United States Patent [19]

Semersky et al.

[11] 4,172,770
[45] Oct. 30, 1979

[54] FLOW-THROUGH ELECTROCHEMICAL SYSTEM ANALYTICAL METHOD

[75] Inventors: Frank E. Semersky; Barry Watson, both of Toledo, Ohio

[73] Assignee: Technicon Instruments Corporation, Tarrytown, N.Y.

[21] Appl. No.: 890,093

[22] Filed: Mar. 27, 1978

[51] Int. Cl.$^2$ .............................................. G01N 27/46
[52] U.S. Cl. ................................ 204/1 T; 204/195 P; 435/817; 435/291
[58] Field of Search ............... 204/195 P, 1 P, 195 B, 204/1 E; 195/127, 103.5 R

[56] References Cited

U.S. PATENT DOCUMENTS

| 2,913,386 | 11/1959 | Clark | 204/195 P |
|---|---|---|---|
| 3,272,725 | 9/1966 | Garst | 204/1 P |
| 3,380,905 | 4/1968 | Clark | 204/195 P |
| 3,622,488 | 11/1971 | Chand et al. | 204/195 P |
| 3,707,455 | 12/1972 | Derr et al. | 204/195 P |
| 3,795,589 | 3/1974 | Dahms | 204/1 T |
| 4,017,374 | 4/1977 | Aas et al. | 204/195 P |
| 4,036,722 | 7/1977 | Brushwyler | 204/195 B |
| 4,073,713 | 2/1978 | Newman | 204/195 B |
| 4,109,505 | 8/1978 | Clark et al. | 73/1 R |

Primary Examiner—G. L. Kaplan
Attorney, Agent, or Firm—S. P. Tedesco

[57] ABSTRACT

An electrochemical system using a flow-through electrode design employing a dual separation method to lower electrode poisoning due to large chemical species and interference current due to small electroactive species is disclosed. The system includes a fluid inlet to a reaction chamber and a fluid outlet from the chamber, with the chamber in contact with an electrode system. The electrode is protected from poisoning and interference by a membrane system comprising a semipermeable membrane having well defined pore ranges therethrough which allow diffusion of only selected size small molecules. A unique sample stream flow control coupled with the size selective membrane combine to remove large, or macromolecule poisoning species and substantially reduce small species interference at the active surfaces of the electrode means.

11 Claims, 4 Drawing Figures

FLOW-THROUGH ELECTROCHEMICAL SYSTEM ANALYTICAL METHOD

BACKGROUND OF THE INVENTION

1. Field of the Invention

This invention relates to an apparatus and method for monitoring the concentration of an electroactive species in a flowing stream of solvent when the electroactive species of interest is present, not in a continuous fashion, but in a discrete high concentration zone or "slug." More particularly, the invention relates to the precise determination of an electroactive species of interest which is in a flowing sample stream which may include two types of contaminating species.

A contaminating species of the first type are large molecules. These are usually molecules in the so-called group of macromolecules. These species could be exemplified by polymer fragments in industrial fluids or blood proteins in biological fluids. These macromolecules are of such a chemistry that they may be absorbed to the surface of an electrode and thereby "poison" the electrode by placing it in an inactive state.

Contaminants of the second type are fundamentally different from contaminants of the first type. This second type of molecules includes small molecules, much the same size as the species of interest whose electrochemical activity we wish to follow. One common example of interfering species is as follows. It is common in the immobilized enzyme art to perform conversions of substrate molecules to hydrogen peroxide (M. W. 34) and measure it polarographically by the oxidation reaction:

$$H_2O_2 \rightarrow 2H^+ + \tfrac{1}{2} O_2 + 2e^-$$

Unfortunately, many biological samples which are of interest also contain significant amounts of uric (M. W. 168 in the keto form) and sometimes ascorbic acid (M. W. 176). Therefore, those systems which operate without a method to exclude these low mass (compared to the macromolecules which have masses on the order of thousands to hundreds of thousands) interfering molecules from the electrode do so with fairly high interference currents being generated. In some cases it is known that the current generated by the interfering species is at least as large as the current of the sample of interest.

Since polarographic methodology is based on additive currents, the species of interest signal may be distorted by the addition of these interference currents to the point where it has no analytical reliability.

2. Description of the Prior Art

In the past, electrode systems have been characterized by a few major types.

The general design of an electrochemical device was shown many years ago by electrodes like the one designed by Leland C. Clark, Jr., and shown in U.S. Pat. No. 2,913,386 entitled "Electrochemical Device For Chemical Analysis." In that system an electrolyte is maintained within a tube-like body electrode by a membrane whose primary function is to maintain the electrolyte with the electrode and to allow diffusable gasses to pass through the membrane.

These electrodes are designed for use in a static sample and have been called "dip-in" electrodes. In use, the electrode's tip is placed in the solution of interest, allowed to remain in the quiet, non-flowing solution until an accurate determination is completed.

This same dipping type electrode is shown in U.S. Pat. No. 3,380,805, also issued to Leland C. Clark, Jr., and entitled "Electrolytic Sensor With Anodic Depolarization." This patent discloses a trielectrode system with a membrane structure which performs much the same function as the membrane of the previously discussed Clark electrode.

These membranes were essentially total liquid barriers, and were not designed and did not function to allow electrolyte to pass the barrier. Rather, as suggested in Clark U. S. Pat. No. 2,913,386, the membranes were typically polyethylene which had the ability to allow gasses to diffuse therethrough, but in no case liquids.

Clearly, these electrodes were not to be used in flowing sample stream systems and they employed liquid nonpermeable membranes to separate solvent of the sample from the captive or internal reference electrolyte.

While the Clark electrodes were primarily for measurement of gasses, due to the nature of their membrane structures, they did allow interfering species of the same physical state as the sample of interest to interfere with the measurement. For example, if the electrode were being used to determine solution $O_2$ levels and there was present a substantial amount of CO or $SO_2$, these interfering species could easily arrive at the electrode, just as the species of interest by permselective crossing of the membrane and generate an interfering current.

Unlike the Clark type electrode, many electrode combinations have been designed to attempt to measure species in a flowing steam.

U.S. Pat. No. 3,622,488, issued to Ramesh Chand entitled "Apparatus For Measuring Sulfur Dioxide Concentrations" shows a system to continuously monitor $SO_2$ concentrations. Again, as in the Clark patents, a membrane is used to eliminate electrolyte loss yet allow diffusion of the $SO_2$ across the membrane to the electrode's surface. While this type electrode does monitor the concentration of $SO_2$ continuously it also has the drawback that interfering species will be allowed to reach the electrode and generate an interference current.

Many solution phase flow-through electrode systems have been demonstrated. In U.S. Pat. No. 3,707,455, issued to D. B. Derr et al., entitled "Measuring System" discloses a captive enzyme reagent. The reagent enzyme is trapped by a membrane. The membrane keeps the larger enzyme molecules inside a chamber and allows small molecules completely free diffusion across the membrane. Even though in a flowing stream, it is clear that small molecule interference in this system is still present, since a dual electrode system is used. One electrode measures species of interest plus interference and one only interfernece.

These systems are subject to the problems inherent in signal conditioning which affect signal reliability. Not only are electrodes like the ones discussed above subject to large molecule poisoning, but since large masses of unnecessary and interfering species arrive at the electrode and are reacted, there are electrodes are subject to more rapid degradation, concomitant failure, and drift. Also since these electrodes do measure large signals occasionally with small contributions from the species of interest, there is the problem of measuring a large volume of response with a small signal of interest and the associated signal-to-noise type problem.

SUMMARY OF THE INVENTION

An object of the present invention is to provide a flowthrough electrochemical system which is capable of measuring a species of interest while reducing the measurement of the interfering species greatly.

Another object of the present invention is to provide for longer electrode life by reducing the amount of poisoning species and interfering species which reach the active surface of the electrode means of the invention.

The objects of the present invention are fulfilled by a flow-through electrochemical system having a first housing which has a fluid inlet and outlet with a reaction chamber therein. The reaction chamber communicates with an electrode receiving chamber. Fluids containing the sample slug are pumped through the reaction chamber by a metering pump. A second housing holds at least an indicating and a reference electrode, which communicate with the reaction chamber through a membrane system. The membrane system segregates large poisoning species on the basis of size and smaller interfering species on the basis of diffusion. The pore size characteristics of the membrane are important in that pores which are too large are inoperative at the fluid flow rates used herein. The electrochemical system of the invention reduces large molecule poisoning as well as lowering small molecule interference by the lessening of interfering current being generated by small molecules reacting at the electrode face.

DETAILED DESCRIPTION OF THE INVENTION

Figure 1:
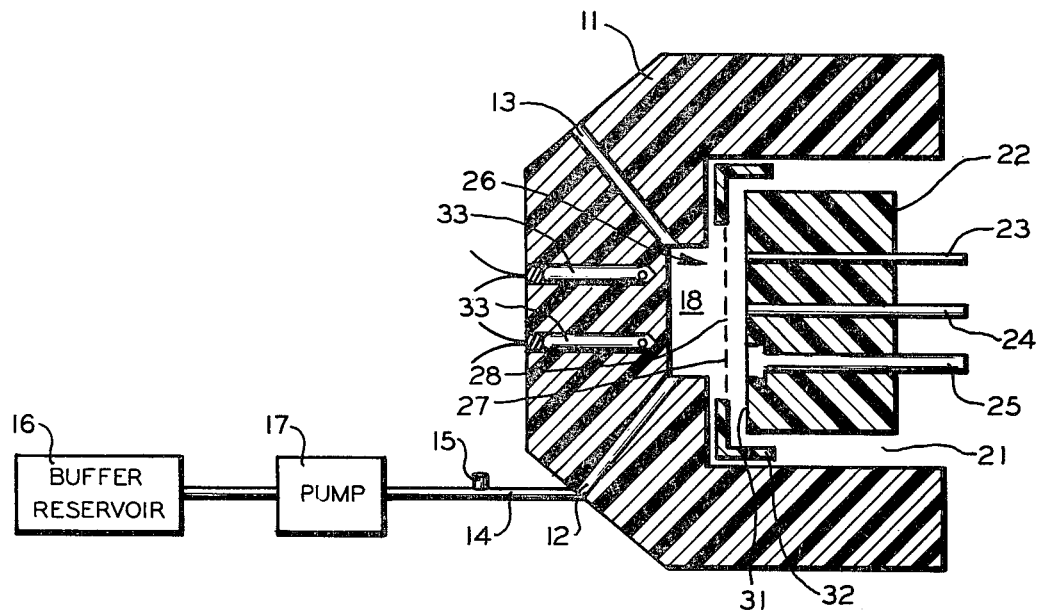
FIG. 1 is a schematic diagram illustrating a cross-sectional view of the electrochemical cell and the flow system used therewith.

FIG. 1 illustrates a preferred embodiment of the present invention. The electrochemical system of the present invention includes a first housing 11 which includes a fluid inlet 12 and a fluid outlet 13. Typically, the fluid inlet 12 is coupled to an inlet line 14 which has integral therewith an injection port 15. Due to the composition of the membrane system used with this invention in the preferred embodiment, a buffer solution must continuously bathe the membrane-electrode system. This continuous buffer solution is provided from a buffer reservoir 16 which supplies a pump 17 which communicates with the fluid inlet 12. The fluid inlet 12 terminates in a reaction chamber 18 which is in communication with the fluid outlet 13 and an electrode receiving chamber 21.

Into the electrode receiving chamber 21 is fitted a second housing 22 which has embedded therein the electrodes which sense the concentration of the electroactive species which pass the membrane system. The electrodes of this system comprise a reference electrode 23, a counter electrode 24 and an indicating or working electrode 25. These electrodes are embedded in the material of the second housing 22 so as to be maintained in a fixed geometric relationship. As seen in FIG. 1, a membrane system 26 comprises in this embodiment of the invention a single layer of a membranous material which allows solvent flow therethrough and thereby selective diffusion across. The membrane 27 has sized pores 28 therein to allow the diffusion. The membrane 27 is retained closely against the face 31 of the electrode by a restraining collar 32. Since many of the species of interest are present in low concentration the electrode response and sensitivity are critical. Thus, a pair of temperature sensing thermistors 33 are embedded into the first housing 11 adjacent the reaction chamber 18 to track the temperature of the reaction buffer solution. As the temperature of the buffer changes the thermistor response is used to recalibrate the electronics package which records and conditions the electrode readings.

As seen in FIG. 1, the sensing tips of the electrodes in the electrode face 31 are in a close spatial relationship with the membrane system 26.

There is always a small space between the electrode face 31 and the membrane system 26. The membranes typically used with the invention must be continuously bathed with fluid to maintain their structural integrity. Thus, buffer flows over the face of the membrane system, diffuses through the pores and bathes the rear face of the membrane, as well as any intervening membrane layers and the electrode face 31. This "wetting" of the membrane system also allows the proper diffusion path to exist between the flowing sample stream and the electrode face. The electrode materials used are typically as follows. The reference electrode 23 is silver-silver chloride electrode, the counter electrode 24 is a platinum electrode as is the indicating electrode 25. The silver-silver chloride reference electrode is preferred so that the buffer can function as a reference electrode filling solution by the incorporation of chloride ions therein. Other types of reference electrodes may be used is appropriate adjustments can be made to the diluent buffer supply.

The three electrode system or so-called potentiostat is preferred to a two electrode system because when there is only a reference and working electrode in the system, current flows through the reference electrode. This can cause variations in the potential difference between the two electrodes due to the IR drop across the sample. Also, when a silver-silver chloride coating is used on a two electrode system reference electrode, the silver chloride coating is eventually depleted by the reduction-oxidation reaction which occurs on the surface of the electrode. So, the use of a two electrode system, even when the two electrodes are very close together, is not favored while the three electrode potentiostat is.

When using the cell of FIG. 1 in a routine laboratory environment, a peak detector and a sampling and hold circuit can be used to measure the maximum current above a base line current and the difference will be proportional to the hydrogen peroxide concentration in the specimen and is, therefore, proportional to the glucose concentration or the similar electroactive species other than hydrogen peroxide.

In the electrochemical cell shown in FIG. 1, the polarographic cell is potentiostatic. This is the so-called "three electrode polarograph" as disclosed in the article, "The Renaissance in Polarographic and Voltammetric Analysis" by Jud B. Flato, appearing in Analytical Chemistry, Vol. 44, September 1972, the disclosures of which are incorporated by reference.

The first and second housing, which holds the electrodes, are made of a rigid, inert, electrically insulating material like glass or plastic. Polymethylmethacrylate has been used quite successfully.

The system operates to reduce poisoning and interference of the indicating, reference, and counter electrode as follows. As the same is injected into the flowing buffer stream, it is considered to be a "slug." Slug is defined herein as a discrete package of the same which travels through the system as a packet without substantial dilution over the time period of the experiment. Many samples of biological origin contain large amounts of contaminating or interfering species like the nonelectroactive macromolecules. Examples of such macromolecules are proteins, nucleic acids or in industrial solutions, polymer and polymer fragments. A second type of interfering species that may be present in biological fluids are smaller electroactive species. When analyzing for the biologically important species glucose, examples of such interfering species are uric acid (M.W. 168) and ascorbic acid (M.W. 176), which are both electroactive.

A membrane found to be particularly suitable for this system is a cellulosic film known as SPECTRAPOR™, and available in films that have molecular mass cutoffs at 12-14,000 mass units, 6-8,000 mass units and at about 3,500 mass units. This membrane shows good long-term stability and is relatively pinhole free. The pores in the membrane perform a separation by size roughly corresponding to the molecular mass of the species. So larger molecules, like proteins, which have masses over 14,000 are excluded by the 12-14,000 membrane, proteins over 3,500 mass units are excluded from passing to the electrode face by the 3,500 cutoff membrane, etc. This process of rough mass exclusion allows for the protection of the electrode from poisoning of the electrode by the adsorption of these large molecules thereon. These membrane films are purchased from Spectrum Medical Industries, Inc., 60916 Terminal Annex, Los Angeles, Calif. 90054.

The membrane also allows for selection of small molecules by a process thought to be diffusion across the membrane system. As the sample slug passes the membrane there is a finite time for diffusion to occur across the membrane through the sized pores. It is known that the smaller a molecule is the faster it diffuses in aqueous solution. Therefore, it has been discovered by the creation of this device that if the flow rate of the sample is matched to the pore size of the membrane it is possible to substantially reduce the amount of one small molecule which reaches the electrode as compared to another small molecule in the same sample. For example, if there is a very large size difference between the species of interest, and the interfering species the flow rate could be lowered to allow more of the small species of interest to arrive at the electrode face. If the interfering species is close in size, and thus diffusion rate, to the species of interest a higher flow rate may be required so that the interfering species is not presented to the membrane system for a long enough time to be appreciably measured. Thus, if there are a number of small interfering species contaminating a sample by adjusting the membrane and flow rate of the sample, it is possible to achieve the partial exclusion of the small interfering species, while allowing the small species of choice to reach the electrode and react therewith.

As the sample slug passes into the reaction chamber 18 and contacts the membrane system, the smallest molecule, i.e., the species of interest, diffuses towards the electrode through the membrane pores. Simultaneously the interfering species begin to diffuse toward the electrode via the membrane pores. The species of interest, being a smaller molecule than the interfering molecules, arrives first at the electrode. As this diffusion toward the electrode is occurring, the sample slug is passing the membrane. As it passes the membrane the concentration of the sample grows smaller and the concentration gradient which was driving the species of interest and the interfering species towards the electrode reverses and the molecules are drawn back into the sample buffer stream. By selecting both the flow rate of the sample past the membrane and the membrane characteristics, the amount of interfering material which reaches the electrode can be very substantially reduced.

Figure 2:
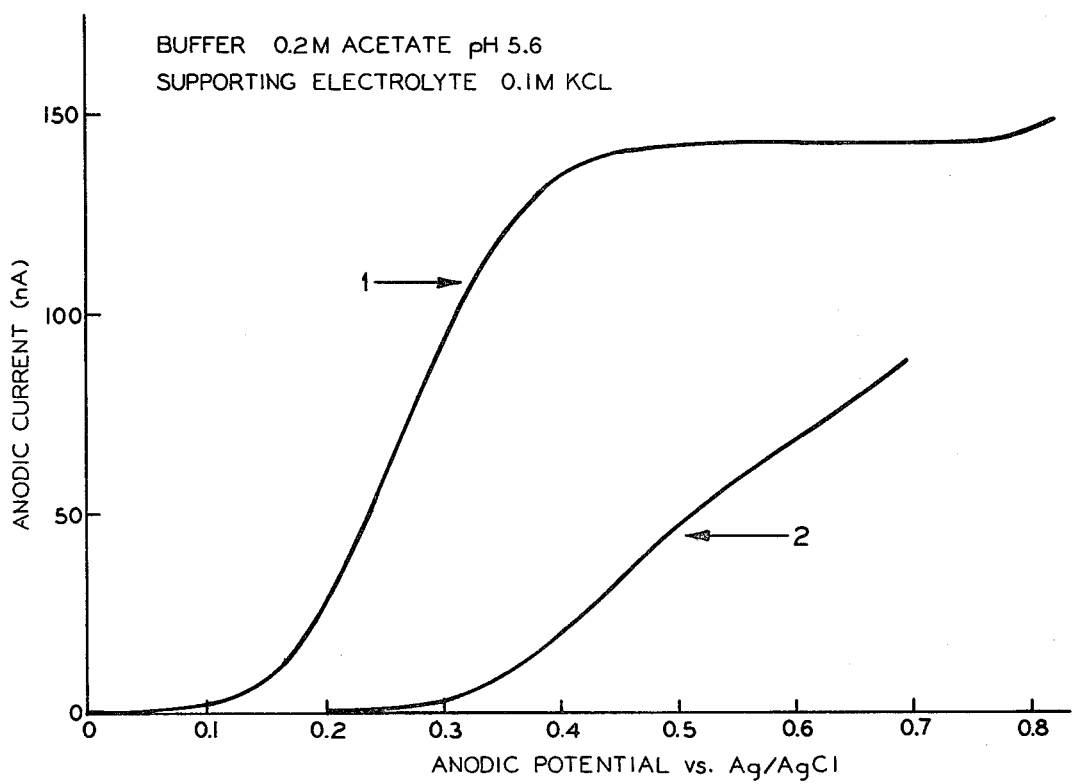
FIG. 2 illustrates the current v. potential curves for a species of interest in the presence of an interfering species.

FIG. 2 shows a plot of anodic current in nanoamperes verses anodic potential referenced to a silver-silver chloride electrode. The graph shows the problem encountered in analyzing a sample using a non-protected electrode and an uncontrolled flow rate. In the example of the plot curve 1 is the oxidation curve for hydrogen peroxide, a species often monitored as an indication of the amount of an enzyme substrate reaction. For example, glucose when reacted with the enzyme glucose oxidase is converted to hydrogen peroxide and gluconic acid. Thus in clinical application, by monitoring the amount of peroxide generated by the enzyme one may back calculate to determine the concentration of the species of interest, glucose. Curve 2 represents the oxidation curve for uric acid, a common interfering species in biological samples.

If the system is being used to monitor hydrogen peroxide (M.W. 34), for example, the uric acid and any contaminating ascorbic acid will undergo an electrochemical reaction at about the same electrode potential as does the peroxide of interest. The main concept of this invention is to control the flow rate of the sample past the membrane system so that the smaller molecule, $H_2O_2$, can diffuse across the membrane system and be measured as the slug passes the reaction chamber but the larger, and therefore slower, interfering molecules cannot.

Note that at low potentials, around $+0.3$ volts, the response due to hydrogen peroxide is high while the response due to uric acids is very low. In the ideal situation the measurement would be made at this low potential to screen out the interference due to uric acid. Since the currents measured by the electrometer would be additive to total current ($i_T$) would equal the current generated by the hydrogen peroxide ($i_{HP}$) and the current due to the oxidation of the interfering species uric acid ($i_{UA}$), thus $$i_T = i_{HP} + i_{UA}$$

Unfortunately, the platinum electrode system preferred for these measurements is not active enough at these low potentials to oxidize completely the hydrogen peroxide. Therefore, the electrode must be operated at between $+0.5$ to $+0.7$ volts for best results and maximum electrode lifetime. As shown by FIG. 2, at this elevated anodic potential both the hydrogen peroxide and the uric acid are substantial contributors to the total signal. Therefore, the use of a membrane system to exclude the uric acid or other interfering species is necessary if accurate, relatively interference free readings are to be made. Since the membrane system excludes a substantial fraction of the interfering species the net current is more accurately a reflection of only the sample of interest and not sample plus interfering species. This exclusion of the interfering species from the electrode differs from presently used systems where the interference is measured by the working electrode and a second electrode and the readings then subtracted. In the case of the present invention the major fraction of the interfering species never reaches the electrode.

Figure 3:
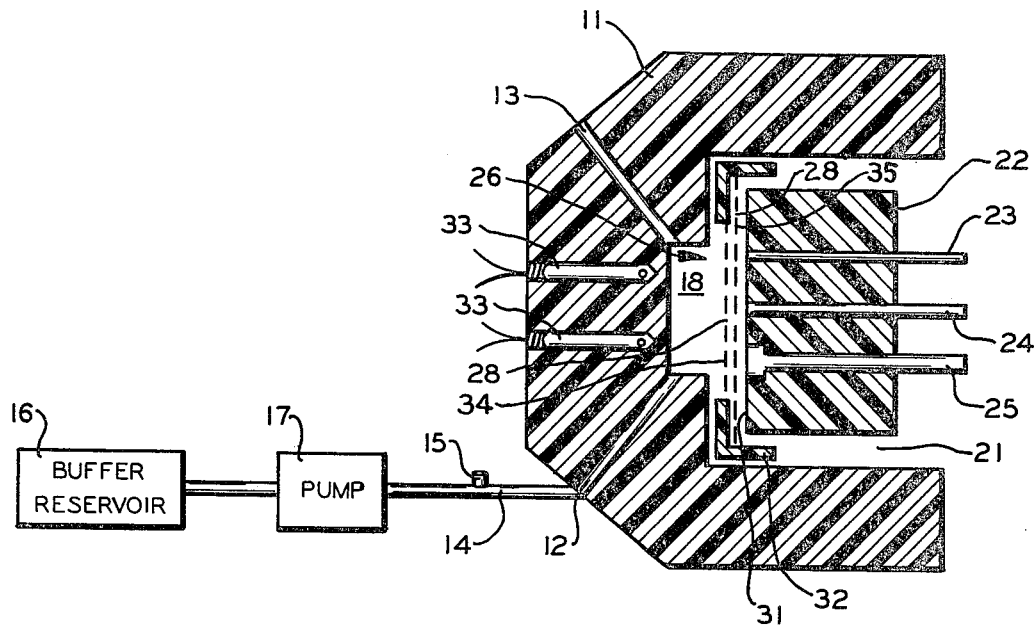
FIG. 3 is a schematic diagram illustrating an alternative embodiment of the invention shown in FIG. 1.

As seen in FIG. 3, the membrane system 26 may comprise a dual membrane having a first membrane 34 and a second membrane 35. The two membrane system prevents the poisoning of the electrode due to any pinhole defects in the single membrane embodiment of FIG. 1. The membrane configuration of FIG. 1, when used with any of the membranes described above, at a controlled flow rate, reduces interference levels below the 5 mg per deciliter level proposed by the Food and Drug Administration. The times typical from injection to sample readout are on the order of 60 seconds with a single membrane and on the order of 70-80 seconds with the dual membrane system. The system allows the effective measurement of glucose levels found in human blood (70-80 mg per deciliter) with less than the 5 mg per deciliter interference fraction proposed by F.D.A.

Figure 4:
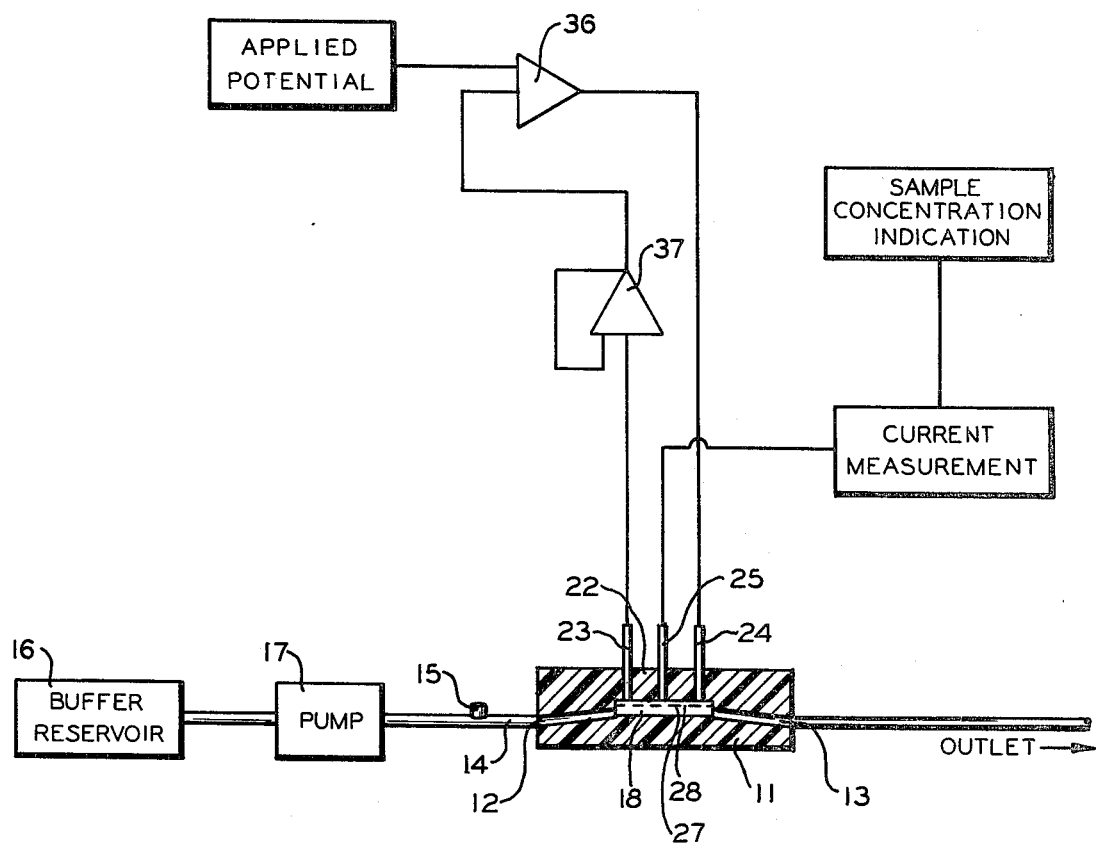
FIG. 4 is a schematic flow diagram illustrating the details of the electrochemical system of the invention.

FIG. 4 shows the system in a flow-through cell using a three electrode system according to the present invention.

The system of FIG. 4 is the same cell as shown in FIG. 1 or FIG. 3. The cell of FIG. 4 is equipped with a reference electrode 23 in the form of a silver wire coated with silver chloride positioned as closely as possible to the indicating electrode 25 which is a platinum wire. The applied potential (+0.6 volts DC) is applied to the input of a control amplifier 36 to which the reference electrode 23 is also connected through voltage follower 37. The output of the control amplifier 36 is connected to the counter electrode 24 which is a platinum wire. By this design essentially no current flows through reference electrode 23 and sufficient compensating potential is applied to counter electrode 24 to maintain the potential difference between the reference electrode 23 and the indicating electrode 25. The indicating electrode 25 is connected to a small conventional current measuring device which provides a current measurement which is converted to the sample equivalent of the original specimen.

According to the present invention the aqueous buffered diluent is continuously pumped through the reaction chamber to both the electrode and membrane, as discussed above. The sample is typically injected from a hypodermic syringe into the injection port which can be in the form of a mixing "tee" covered with a rubber diaphragm.

The electrode response from the measurement of the electroactive species of interest is measured by a current measuring device such as a current follower. This value is then converted to the sample equivalent of the original specimen. In the case of biological material the samples are reported as mg percent for example a glucose equivalent of an original specimen is usually reported in mg glucose/100 ml (i.e., mg percent) of specimen. These units are conventional in clinical applications.

In addition to buffer it is desirable to add salts such as potassium chloride or sodium chloride which serve to establish the reference potential when silver-silver chloride reference electrodes which use the buffer as a filling solution are employed. A bacterial inhibitor can be incorporated in the buffered diluent to retard bacterial interference. For a detailed description of the current measuring system used herein reference is made to copending U.S. patent application Ser. No. 477,922 by D. Gray et al. entitled "Glucose Analyzer."

An example of the system parameters are as follows. When the system is being used to detect hydrogen peroxide from the oxidation of glucose by glucose oxidase, an aliquot of 2.5 microliters of sample is introduced into the flowing buffer stream that flows at a rate of between 0.1 to 5 ml per minute. While, as discussed above, the flow rate must be adjusted for each sample and membrane system, it appears that for a sample containing about 100 mg per deciliter glucose, when the glucose is converted to hydrogen peroxide and a 2.5 microliter sample is used, a flow of 0.1 to 2 ml per minute gives the optimum electrode response. It has been discovered that if the double layer membrane system of FIG. 3 is used a flow rate of one ml per minute gives good electrode response. The double layer system comprises two circular sections of a 12-14,000 atomic mass unit cutoff membrane of SPECTRAPOR $2^{TM}$ purchased from Spectrum Medical Industries, Inc. While with some combinations of interfering species a membrane with smaller pore sizes may be preferred. This double layer of 12-14,000 cutoff membrane material functions well over a wide range of flow rates. The time from injection, through sample peak to stable base line is as indicated above about 70-80 seconds.

It should be noted that while SPECTRAPOR$^{TM}$ membranes are used in the system, tests on Millipore$^{TM}$ membranes, type VS, VM and PSAC have proven acceptable if flow rates are adjusted to match the membrane. The Millipore$^{TM}$ membranes exclude in the mass range of 500-1000 mass units. It has been shown that of all membranes tested, cellulosic membranes give continuously high quality results for long periods of use. Also, as membrane types are modified or changed totally, the loss of signal strength from the electrode may be compensated for by changing the working surface area of the electrode.

To determine the usefulness of the system in determining a sample biological unknown the substance glucose was chosen. The glucose sample was passed through a glucose oxidase cartridge and the resultant hydrogen peroxide was monitored in the presence of the F.D.A. reference interferents. Table I shows the results of the interference studies. Table I includes three columns, one describing the interfering substance, the remaining two columns represent the results from two different instruments. To demonstrate that the system works well under different service conditions, two instruments were similarly equipped and numerous samples of varied composition were analyzed by the separate instruments. Then, the different instruments having been subjected to different aging conditions, were used to analyze identical sample fractions as described below. The results show that while some variance is experienced between the two instruments, that in all, the interference levels are kept below the recommended minimum.

To perform the test a sample of human serum was divided into two fractions. The amount of glucose was determined. For example, a serum sample would show about 100 mg/dl of glucose. The halves are about 5 ml each. Enough solid or solution phase interferent is added to one-half of the sample to bring the blood-interferent solution to the concentration indicated in parenthesis under the "SUBSTANCE ADDED" column. Enough water, buffer or solvent is added to the second-half of the serum to match its volume to that of the first one-half of the serum sample. The samples are run on two instruments. The difference between the two results for the same sample are probably due to; (1) individual differences between platinum electrodes and (2) age and condition of the membrane system. Notice that some samples show negative "BIAS" results. To determine the "BIAS" the samples are run, the real or "true" glucose value is determined from the second-half sample. The first-half sample is run and the value of its glucose equivalent is subtracted from the second-half reading. For example, if the glucose concentration were 100 mg/dl and the interference+glucose sample readings 101.6 mg/dl the BIAS is +1.6, as shown in "INSTRUMENT 1", item 1.

Some samples show a negative bias. This is thought to be due, in one case, to latent catalase enzyme in the sample which destroys hydrogen peroxide during the course of the test and artificially lowers the "BIAS."

TABLE I
INTERFERENCE STUDY (a) ENDOGENOUS SUBSTANCES

| SUBSTANCE ADDED (mg/dl) | BIAS (mg/dl) INSTRUMENT 1 | INSTRUMENT 2 |
|---|---|---|
| Fructose (150) | +1.6 | 0 |
| Mannose (300) | +2.8 | +4.1 |
| Galactose (300) | +1.2 | +0.3 |
| Ascorbic Acid (25) | +3.4 | +1.8 |
| Creatinine (25) | +0.4 | −0.2 |
| Glutathione (50) | +1.8 | +1.6 |
| Citric Acid (1500) | −3.8 | −4.4 |
| Hemoglobin (5000) | −4.8 | −2.6 |
| $NH_4Cl$ (1) | −1.2 | +0.6 |
| Bilirubin (25) | 0 | 0 |
| Uric Acid (25) | +1.0 | +3.4 |
| Cysteine (40) | +2.0 | +3.6 |
| Lipid (600) | | +1.6 |

(b) EXOGENOUS SUBSTANCES

| SUBSTANCE ADDED (mg/dl) | BIAS (mg/dl) INSTRUMENT 1 | INSTRUMENT 2 |
|---|---|---|
| L-Dopa (10) | +1.0 | +2.2 |
| Xylose (150) | +1.8 | +0.2 |
| Ribose (150) | +1.2 | +0.8 |
| Na Salicylate (50) | +1.0 | +0.2 |
| Na Diatrizoate (5% v/v) | +0.6 | +0.6 |
| Meglumine diatrizoate | +1.6 | +0.8 |
| Tolbutamide (25) | −0.8 | 0 |
| Methyl Dopa (25) | +3.0 | +2.8 |
| Steptomycin (30) | −0.6 | +1.0 |
| Sulfadiazine (50) | +2.2 | +1.0 |
| Dextran (100% of plasma volume) | +2.4 | +1.6 |
| Acetyl Salicylic Acid (30) | +0.2 | 0 |

(c) ANTICOAGULANTS AND PRESERVATIVES

| SUBSTANCE ADDED (mg/dl) | BIAS (mg/dl) INSTRUMENT 1 | INSTRUMENT 2 |
|---|---|---|
| Na Fluoride (750) | +2.4 | +2.5 |
| Na Heparin (7000 Vldl) | −0.6 | +0.4 |
| Thymol (500) | −4.8 | −2.8 |
| E.D.T.A. (550) | +0.2 | +1.2 |
| Na Oxalate (800) | | +1.0 |
| Na Citrate (2100) | +2.2 | +3.8 |

The day-to-day precision evaluated from results for aqueous glucose standards and stable serum are seen in Table 2 (a) and (b). In every case, the system, with results for two test instruments, showed reproducibility as the coeffient of variation (c.v.%) of less than 2%. This is well below the 5% considered acceptable for most clinical uses.

TABLE 2
PRECISION (a) AQUEOUS STANDARDS (Prepared from NBS reference material SRM No. 917)

| TRUE VALUE | INSTRUMENT 1 MEAN | S.D. | C.V.% | INSTRUMENT 2 MEAN | S.D. | C.V.% |
|---|---|---|---|---|---|---|
| 50 | 49.3 | 0.66 | 1.3 | 50.0 | 0.73 | 1.5 |
| 100 | 99.7 | 1.38 | 1.4 | 99.6 | 0.69 | 0.7 |
| 350 | 345.7 | 2.90 | 0.8 | 345.4 | 2.7 | 0.8 |

(b) SERUM POOLS

| POOL | INSTRUMENT 1 MEAN | S.D. | C.V.% | INSTRUMENT 2 MEAN | S.D. | C.V.% |
|---|---|---|---|---|---|---|
| Low | 51.6 | 0.95 | 1.8 | 51.6 | 0.76 | 1.5 |
| Normal | 125.5 | 2.04 | 1.6 | 124.1 | 1.59 | 1.3 |
| High | 336.9 | 3.88 | 1.2 | 333.5 | 2.40 | 0.7 |

Therefore, clearly the unique flow-through system using a semi-permeable membrane system lowers and in some cases eliminates interference when measuring electroactive species.

In accordance with the provisions of the patent statutes, the principle and mode of operation of the invention has been explained, and we have illustrated and described in the typical embodiment what is considered its best embodiment. It is understood that, within the scope of the appended claims, the invention may be practiced otherwise than as specifically illustrated and described in the typical embodiment and accompanying alternatives herein.

We claim:

1. A method of determining the solution concentration in a sample liquid stream of an electroactive species in the presence of at least one interfering electroactive species comprising placing an electrode means adjacent a flow-through type reaction chamber; subsequently separating said electrode means from said reaction chamber by a membrane system comprising at least one layer of a membrane material which has pores therethrough which allow selective diffusion across said membrane system, said membrane material permitting diffusion therethrough of said at least one interfering electroactive species at a lower rate than said electroactive species; subsequently flowing a sample stream adjacent to said membrane system at a predetermined flow rate to allow diffusion of said electroactive species from said reaction chamber to said electrode means to the substantial exclusion of said at least one interfering electroactive species;

monitoring the response of said electrode means; and flowing a buffer stream adjacent to said membrane to allow diffusion of said electroactive species and said at least one interfering electroactive species into said buffer stream preparatory to the flowing of a different sample liquid stream adjacent said membrane for determining the solution concentration of said electroactive species therein.

2. The method of claim 1 wherein said electrode means includes an indicating, reference and counter electrode.

3. The method of claim 1 wherein said membrane system includes a single layer of membrane material of a cellulosic film having sized pores therethrough to affect a molecular mass diffusion cutoff.

4. The method of claim 3 wherein said membrane has a molecular mass diffusion cutoff of 12–14,000 atomic mass units.

5. The method of claim 3 wherein said membrane has a molecular mass diffusion cutoff of 6–8,000 atomic mass units.

6. The method of claim 3 wherein said membrane system has a molecular mass diffusion cutoff of about 3,500 atomic mass units.

7. The method of claim 1 wherein said membrane system includes a double layer of said membrane material with a molecular mass diffusion cutoff of 12–14,000 atomic mass units.

8. The method of claim 1 wherein said membrane system includes a double layer of said membrane material with a molecular mass diffusion cutoff of 6–8000 atomic mass units and with said layers being in close contact with each other.

9. The method of claim 1 wherein said membrane system includes a double layer of said membrane material with a molecular mass diffusion cutoff of about 3,500 atomic mass units and with said layers being in close contact with each other.

10. A method of electrochemically measuring the concentration of relatively low mass electroactive species of interest in a sample stream in the presence of high and low mass interfering species, comprises the steps of:

providing a flow path over a membrane protected electrode means wherein said membrane has a molecular mass diffusion cutoff such that said high mass molecules with masses higher than the molecular mass cutoff are excluded from the electrode; then precisely controlling the flow rate of said sample stream so that the diffusion ratio of the low mass interfering species and the low mass electroactive species of interest is such that substantially all of said low mass interfering species is excluded from said electrode means; then measuring the response of said electrode means to the electrochemical reaction of said low mass species of interest at said electrode means.

11. The method according to claim 10 wherein said species of interest is hydrogen peroxide derived from the conversion of glucose to gluconic acid and hydrogen peroxide.

* * * * *